(12) United States Patent
Rontal

(10) Patent No.: US 7,522,955 B2
(45) Date of Patent: Apr. 21, 2009

(54) METHOD AND APPARATUS FOR THE ULTRASONIC CLEANING OF BIOFILM COATED SURFACES

(76) Inventor: Michael Rontal, 3639 Shoreview Ct., Bloomfield Hills, MI (US) 48302

( * ) Notice: Subject to any disclaimer, the term of this patent is extended or adjusted under 35 U.S.C. 154(b) by 260 days.

(21) Appl. No.: 11/257,198

(22) Filed: Oct. 24, 2005

(65) Prior Publication Data

US 2006/0069343 A1 Mar. 30, 2006

Related U.S. Application Data

(63) Continuation-in-part of application No. 11/004,392, filed on Dec. 3, 2004, which is a continuation-in-part of application No. 10/955,173, filed on Sep. 30, 2004.

(60) Provisional application No. 60/508,824, filed on Oct. 3, 2003.

(51) Int. Cl.
*A61N 1/30* (2006.01)

(52) U.S. Cl. ............... 604/20; 604/19; 604/22; 604/35; 604/46; 604/500; 606/27; 601/2

(58) Field of Classification Search ............. 604/19–22, 604/500, 35, 46–48, 93.01, 95.05, 131; 606/27–28; 601/2

See application file for complete search history.

(56) References Cited

U.S. PATENT DOCUMENTS

| 581,129 | A | 4/1897 | Nevius | |
|---|---|---|---|---|
| 1,505,654 | A | 8/1924 | Macbeth | |
| 2,234,995 | A | 3/1941 | Waechter | 240/59 |
| 3,882,490 | A | 5/1975 | Tashiro et al. | 340/366 B |

(Continued)

OTHER PUBLICATIONS

Costerton et al. "Bacterial Biofilms: A Common Cause of Persistent Infections" Science, 284:1318-1322 (1999) (abstract).

(Continued)

*Primary Examiner*—Nicholas D Lucchesi
*Assistant Examiner*—Quynh-Nhu H Vu
(74) *Attorney, Agent, or Firm*—Gifford, Krass, Sprinkle, Anderson & Citkowski, P.C.

(57) ABSTRACT

To treat body surfaces, such as the sinuses, which are coated with biofilms, the surface is irrigated and suctioned with a fluid which may contain a biocide or other chemical agent for disrupting the biofilm while ultrasonic energy is applied to either the fluid barrier formed over the biofilm or a body surface proximal to the biofilm. Action of the fluid enhanced by the ultrasonic energy tends to remove sections of biofilm which are suctioned out of the site. An electrical field may also be applied to the biofilm to enhance the disruptive action. Apparatus for practicing this method to treat chronic rhinosinusitis comprises an elongated tube adapted to be inserted into sinus cavities through the nose or mouth. The tube includes a first lumen which feeds an irrigating fluid containing biocides and/or biofilm-disruptive chemicals to the treatment site and a second lumen which suctions fluid from the site. An ultrasound horn extends through the tube and its distal end introduces ultrasonic energy into the fluid layer overlying the biofilm. Alternatively, an ultrasound probe may be applied to an adjacent body surface, such as the face over a sinus cavity. In an alternative embodiment, the tube includes a pair of electrodes which establish an electric field across the biofilm, accelerating degradation.

6 Claims, 7 Drawing Sheets

U.S. PATENT DOCUMENTS

| | | | | |
|---|---|---|---|---|
| 3,906,216 | A | | 9/1975 | Eriksson .................. 240/6.4 W |
| 4,211,955 | A | | 7/1980 | Ray ............................ 315/53 |
| 4,797,793 | A | | 1/1989 | Fields ........................ 362/105 |
| 5,058,900 | A | | 10/1991 | Denen ......................... 273/416 |
| 5,163,433 | A | * | 11/1992 | Kagawa et al. ................... 601/2 |
| 5,307,816 | A | * | 5/1994 | Hashimoto et al. ........... 600/439 |
| 5,312,813 | A | | 5/1994 | Costerton et al. .............. 514/29 |
| 5,385,938 | A | | 1/1995 | Yu et al. ..................... 514/557 |
| 5,389,677 | A | | 2/1995 | Yu et al. ..................... 514/557 |
| 5,422,370 | A | | 6/1995 | Yu et al. ..................... 514/557 |
| 5,462,644 | A | | 10/1995 | Woodson .................... 204/131 |
| 5,628,761 | A | | 5/1997 | Rizik .......................... 606/170 |
| 5,728,124 | A | | 3/1998 | Cockburn et al. ............. 604/22 |
| 6,168,288 | B1 | | 1/2001 | St. Claire .................... 362/184 |
| 6,258,249 | B1 | | 7/2001 | Simpson ..................... 205/687 |
| 6,283,610 | B1 | | 9/2001 | Alajajian .................... 362/199 |
| 6,293,957 | B1 | * | 9/2001 | Peters et al. ................ 606/167 |
| 6,485,160 | B1 | | 11/2002 | Sommers et al. ............ 362/184 |
| 6,517,215 | B2 | | 2/2003 | Mele .......................... 362/203 |
| 6,578,994 | B1 | | 6/2003 | Beyerlein ................... 362/490 |
| 6,623,444 | B2 | * | 9/2003 | Babaev ........................ 604/22 |
| 6,762,160 | B2 | | 7/2004 | Barbeau et al. ............. 510/161 |
| 2004/0073151 | A1 | * | 4/2004 | Weston ........................ 602/41 |
| 2004/0151716 | A1 | | 8/2004 | Hamer et al. ............ 424/94.63 |
| 2005/0038376 | A1 | * | 2/2005 | Zumeris et al. ............... 604/22 |
| 2005/0075621 | A1 | * | 4/2005 | Rontal ........................ 604/500 |
| 2005/0080396 | A1 | * | 4/2005 | Rontal ........................ 604/500 |
| 2006/0224103 | A1 | * | 10/2006 | Rontal ......................... 604/22 |

OTHER PUBLICATIONS

Huang et al. "Effects of Ultrasonic Treatment on the Efficacy of Gentamicin against Established *Pseudomonas aeruginosa* Biofilms" Colloids and Surfaces B: Biointerfaces 6:235-242 (1996) (abstract).

Mayo Clinic College of Medicine "Fruits of a Creative Mind: A Clearer Picture" (May 11, 2004).

Rediske et al. "Ultrasonic Enhancement of Antibiotic Action on *Escherichia coli* Biofilms: an In Vivo Model" Antimicrobial Agents and Chemotherapy, vol. 43, pp. 1211-1214 (May 1999).

Burnett "Pocket Monsters: the nature of your enemy" from Parkell. com website (undated).

Oulahal-Lagsir N, Martial-Gros A, Bonneau M, Blum LJ "*Escherichia Coli* -Milk" Biofilm Removal From Stainless Steel Surfaces: Synergism Between Ultrasonic Waves and Enzymes pp. 1-2.

Ashland Sonoxide ™ Ultrasonic Water Treatment pp. 1-2.

Rediske, A.M., Pitt, W.G. Ultrasonic Enhancement of Antibiotic Action on *Escherichia Coli* Biofilms: An In Vivo Model pp. 1-11.

Journals from Cambridge University Press Biofilms pp. 1-2.

Montana State University Effects of Ultrasonic Treatment on the Efficacy of Gentamicin Against Established *Pseudomonas Aeruginosa* Biofilms p. 1.

Andrea M. Rediske, Weston C. Hymas, Rachelle Wilkinson, William G. Pitt, "Ultrasonic Enhancemnet Of Antibiotic Action on Several Species of Bacteria", J. Gen. Appl. Microbiol., vol. 44, p. 283-288, 1998.

Andrea M. Rediske, Beverly L. Roeder, Jared L. Nelson, Rachel L. Robison, G. Bruce Schaalje, Richard A. Robison, William G. Pitt, "Pulsed Ultrasound Enhances the Killing of *Escherichia Coli* Biofilms by Aminoglycoside Antibiotics in Vivo", Antimicrobial Agents and Chemotherapy, vol. 44, p. 771-772, 2000.

* cited by examiner

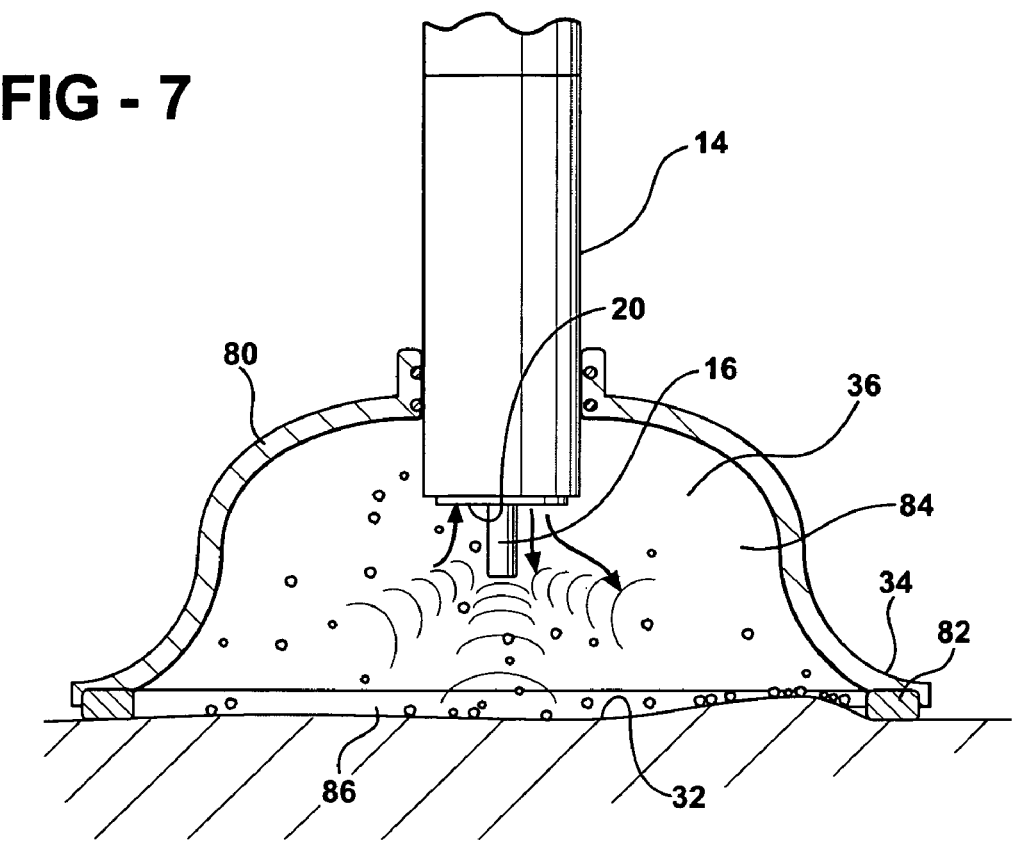
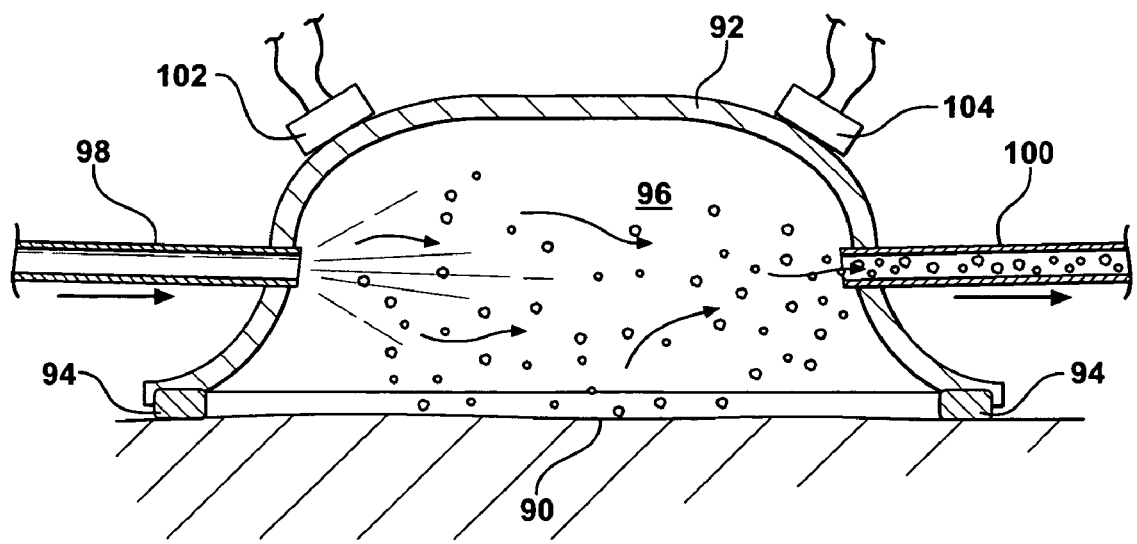

METHOD AND APPARATUS FOR THE ULTRASONIC CLEANING OF BIOFILM COATED SURFACES

RELATED APPLICATIONS

This application is a continuation-in-part of U.S. patent application Ser. No. 11/004,392 filed Dec. 3, 2004, which is a continuation-in-part of U.S. patent application Ser. No. 10/955,173 filed Sept. 30, 2004, which claims priority of U.S. Provisional Patent Application Ser. No. 60/508,824 filed Oct. 3, 2003, which is incorporated herein by reference.

FIELD OF THE INVENTION

This invention relates to methods and apparatus for the ultrasonic cleaning of bodily tissues coated with biofilm and more particularly, to such method and apparatus employing irrigation of the biofilm and the application of ultrasonic energy to the biofilm.

BACKGROUND OF THE INVENTION

Bacteria may exist within a fluid media in a planktonic state or may form on a surface bounding the fluid medium in a conglomerate of microbial organisms termed a biofilm. In the biofilm, the bacteria live at a lower metabolic state than when in planktonic form and exude a hydrated matrix of exopolymers, typically polysaccharides, and other macromolecules. Bacteria in the biofilm form strong chemical bonds with surface carbohydrate moieties. The exopolymers encase the bacteria in a manner that leaves tunnels or channels through which the overlying fluid medium can circulate. In this way, the bacteria are protected from the dangers of the fluid medium, can receive nutrients, and rid themselves of waste. The protective film formed as part of a biofilm shields the bacteria from the action of antimicrobials and like therapeutic agents at concentrations which would otherwise normally affect the bacteria.

The bacteria in this unique metabolic state affect other bacteria in the region to produce a coordinated lifestyle. This process is termed "quorum sensing."

Biofilms may be formed on the surface of any living tissue, as well as foreign bodies, such as heart valves and the like, which are maintained in association with human tissues. When the biofilm is formed on living tissue, the biochemical products and toxic wastes it secretes may affect the tissue surface to produce an inflammatory state and areas of chronic infection, such as chronic ear disease, osteomyelitis, chronic tonsillitis, prostatitis, vaginitis, and calculi, as in the kidney. In many cases, chronic sinusitis appears to be an inflammatory disease of the lining mucosal, rather than the disease of bacteria-invading tissue. I have conducted electron microscopic studies that show biofilm exists on the mucosal blanket overlying the cilia extending from sinus tissue. Collateral damage from the immune interaction between the biofilm products and the associated tissue would be the basis of the inflammatory mucositis seen in chronic rhinosinusitis.

The biofilm insulates the embedded bacteria from biocides contained in the proximal fluid layer so that normal concentrations of antibiotics or the like, which would kill the bacteria if they were in a planktonic state, have little or no effect on the bacteria of a biofilm. Antibiotic concentrations of 1000 to 2000 times higher than possible with systemic applied antibiotics would be required to destroy the bacteria of a biofilm.

Past efforts to disrupt the biofilm by breaking it up or killing the bacteria have included treatment with chemical compounds such as antibiotics, chemical agents directed at dissolving or breaking up the polysaccharide binders such as surfactants, enzymes, denaturing agents, and the like. In the dental field, the most effective treatment has been found to be scraping and debriding with mechanical instruments. Efforts have also been made to use ultrasonic energy to either increase the metabolic rate of the underlying bacteria so that they better absorb antibiotics and the like, or to mechanically disrupt the biofilm encasement by the mechanical bursting of micro-bubbles induced by ultrasonic energy sources. It has also been suggested that electric fields imposed across the biofilms or the fluid layers in contact with the biofilm will enhance break-up or electrophoretically drive biocides into the bacteria encased in the layers.

SUMMARY OF THE INVENTION

The present invention is accordingly directed toward a method of removing biofilms in general, and particularly from living tissue, and more particularly from body cavities that are coated with biofilm, by flowing fluid containing various biofilm-active agents against the biofilm and suctioning the fluid from the area. Simultaneously ultrasonic energy is applied to the biofilm either by a probe inserted into the fluid layer or by application through body tissues from a remote location. The fluid irrigation is introduced under pressure and withdrawn by a suctioning action to introduce the disruptive materials to the biofilm and the ultrasound produces shear forces which tend to tear off portions of the film and withdraw them from the treatment area.

This irrigation-suction action creates a fluid film over the biofilm and the ultrasonic energy acts to mechanically drive the fluid into the film and produce micro-bubbles in the fluid which release energy upon bursting and mechanically disrupt the fluid. Alternatively, the ultrasonic energy may increase bacterial metabolism leading to susceptibility to deranging protein synthesis or cell division. In certain embodiments of the invention which will subsequently be described in detail, this irrigation/suction accompanied by the introduction of ultrasonic energy into the resulting film may be accompanied by electric fields imposed across the biofilm or the fluid interfacing the biofilm and/or mechanical scrubbing, to further enhance the breakup of the biofilm.

These actions to disrupt the biofilm are all designed in such a way as to neither destroy nor unduly stress the underlying tissue. In an in vitro experiment sinus tissues covered by a mucus blanket harboring a biofilm were treated by irrigation and suction and ultrasonic energy was introduced by a probe immersed in the fluid layer covering the tissue. In another experiment the ultrasonic energy was introduced through the wall of the fluid container. In both cases the ultrasonic energy and irrigation shattered and removed the biofilm and the cilia growing from the tissue remained intact.

A preferred embodiment of the apparatus for practicing the present invention, which will subsequently be described in detail, comprises an elongated tube or barrel, adapted to be introduced to the human body through the nasal passages or otherwise, so that its distal end is in proximity to a biofilm-lined sinus to be treated. The tube may be rigid or flexible, straight or bent, and includes a first lumen for introducing pressurized bio-treatment fluid at the proximal end so that it passes through the tube and exits at the distal end. The discharge may be through a nozzle to produce a high-velocity spray. A second lumen is connected to a vacuum source at the proximal end so as to create a suction at the distal end to remove excess fluid along with debris, including fragments from the biofilm and secretions from the sinuses. Both the irrigation of the bio-affecting fluid and its suctioned removal may be continuous or intermittent, controlled by valves. This allows the introduction of fluid pressure waves by the alternate introduction of pressured fluid and its suctioned removal.

The distal section of the tube may be manually deformable to allow the surgeon to conform the tube to particular applications. This distal section may be removable from the main section of the apparatus to allow replacement with a sanitary, unbent section.

In an alternative embodiment of the invention the ultrasonic energy is introduced to the distal end of the application tube by introducing the ultrasound into the proximal end of the irrigating lumen so that the fluid column in the tube carries the ultrasonic forces to the treatment area, eliminating the need for an ultrasound horn formed along the length of the apparatus.

In an alternative embodiment of the invention, the biofilm affected tissue may be encased in a chamber having open resilient edges which bear against the tissue at its boundaries; the bio-affecting fluid is then introduced and removed from the chamber and ultrasonic forces are imposed on the fluid contained within the chamber, and bearing against the biofilm, either by a ultrasonic horn projecting into the fluid-filled cavity, or by the application of ultrasonic forces to the wall of the chamber.

The biofilm encasing chamber may either be formed at the end of an elongated tube containing the fluid lumens and the ultrasonic horn, or as a separate device which may be applied to external body parts, such as skin burns.

In still another embodiment of the invention the ultrasonic energy is introduced to the biofilm through the surrounding body structure by applying energy from an ultrasound probe into a body surface proximal to the biofilm, through a bag of fluid bearing against that surface. In treating sinusitis the probe may be positioned on the patient's face nearest the sinus being irrigated. The ultrasonic vibrations pass through the facial bones and tissue and stimulate the biofilm.

Other objectives, advantages and applications of the present invention will be made apparent by the following detailed description of several embodiments of the invention. The descriptions make reference to the accompanying drawings in which:

BRIEF DESCRIPTION OF THE DRAWINGS

FIG. 7 is a view, partly in section, of an alternative form of the apparatus of the present invention including a cavity adapted to surround the treatment area;

FIG. 8 is another alternative embodiment of the apparatus of the present invention including a cavity adapted to surround the treatment area and having inlet and outlet ports for the bio-reducing agent and means for introducing ultrasonic energy through the wall of the cavity.

DETAILED DESCRIPTION OF THE INVENTION

Figure 1:
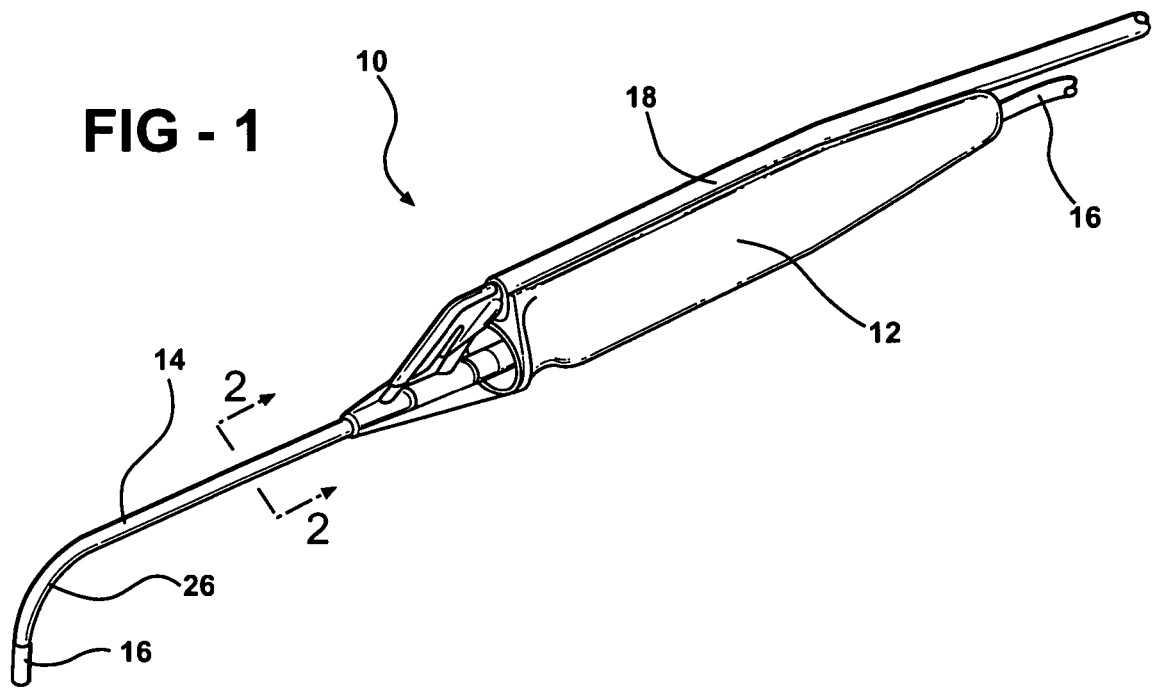
FIG. 1 is a perspective view of a handheld instrument, formed in accordance with the present invention, for practice of the inventive method.

The method of the present invention broadly involves treatment of a body tissue or bodily implant or prosthesis having a biofilm coating on its surface by irrigating the surface with a flow of fluid and suctioning the excess fluid off while imparting energy to the biofilm directly or through the fluid to reduce or change the biofilm. The irrigating fluid preferably contains a bio-reducing agent which will reduce or disrupt the biofilm by destroying its integrity or damaging the constituent bacterial cells. These agents may include surfactants, proteases, enzymes, denaturing agents, and the like. They may include biocides such as antibiotics and antifungal agents.

The chemical agents which may disrupt and destroy the biofilm include guaifenesin, dornase alfa and N-acetylcysteine. These materials are particularly advantageously used in a preferred embodiment of the invention in which the biofilm and mucus coats the sinuses. Guaifenesin is a mucolytic and is often used for the treatment of sinusitis and rhinitis. Dornase alfa (ymogen) is used to treat the thick mucus of cystic fibrosis and N-acetylcysteine is used for excess mucus in chronic bronchitis. They are known to break up mucus which is involved in biofilm infections and may act on the biofilm itself. Thus, the use of these chemicals in the method of the present invention performs a synergistic role in simultaneously treating the underlying mucosal tissues and reducing the integrity of the overlying biofilm.

Any other bio-reducing or biocide drugs or combinations thereof may be used in a particular application.

The ultrasonic energy imparted into the fluid film covering the biofilm, in the practice of the present invention, may be of a sinusoidal or pulsed character. The ultrasonic signal is generated by a unit that is external of the body. The generator may be of a fixed frequency or it may scan a range of frequencies continually to ensure optimum coupling of energy through the fluid layer into the biofilm. The exact manner in which ultrasonic forces enhance destruction of biofilm may involve the physical agitation of the minute bubbles produced by the ultrasound in the overlying fluid. Bursting of these bubbles produces forces that may cause tears in the biofilm, Alternatively, the ultrasonic energy may increase the metabolism of the bacteria in the biofilm, increasing its susceptibility to the biocides and bio-reducing agents in the irrigating fluid. The energy of the ultrasound must be limited to avoid damage to the underlying tissues, and values as high as 250 watts per square centimeter are apparently safe. This device is not designed to destroy mucosal tissue. Relatively low frequencies have been found more effective than higher frequencies in ultrasonic treatment of biofilm and 10 kHz-100kHz may be a reasonable range of application. In in vitro experiments I have used 35 kHz successfully.

In those embodiments of the invention in which an electric field is applied across either the microfilm or the fluid layer overlying the microfilm, either AC or DC may be applied. The DC may be pulsed so that rapid changes in the field gradient induce tearing forces in the biofilm.

A preferred embodiment of an instrument for use in practice of the present invention is illustrated in FIG. 1. The instrument, generally indicated at 10, has a handle section 12 for manual support and manipulation of the device and an elongated application tube or barrel 14 extending from the handle and terminating in a distal end 16. The tube 14 may be rigid and may be straight or formed with a bend along its length. Alternatively, it may be made of a manually deformable material and may be bent as needed for application into a body cavity. The distal end of the tube 14 may be removable from the handle 12 for replacement.

A pair of conduits 18 extend along the handle and connect at their proximal end to a source of the bio-affecting irrigating fluid and to a sink for the suctioned fluid (not shown). The fluid is pumped outwardly from the proximal end from a source in one conduit and is then carried by the other conduit back from the irrigated source to the proximal end.

Figure 2:
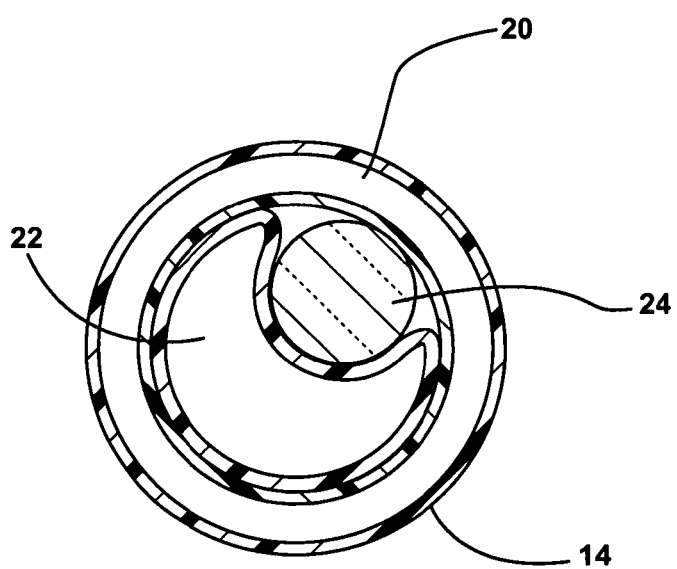
FIG. 2 is a cross-sectional view of the tube of the handheld tool of FIG. 1, taken along line 2-2 of FIG. 1.

The pump which feeds the irrigating fluid to the instrument 10 and the suction device that retrieves it from the irrigated area may feed from the same sump with an appropriate filter in the return line to remove solid matter contained in the fluid. Alternatively, the fluid may not be reused and the irrigated fluid may be discarded. The two conduits 18 feed to lumens in the tube section 14. As is best seen in the cross section of FIG. 2, the irrigating fluid may pass through a lumen 20 which is concentric about the tube 14 along its length and return through a larger lumen 22. An ultrasound horn 24 carries energy from a generator 50 (FIG. 4) at the proximal end to the distal end.

Figure 9:
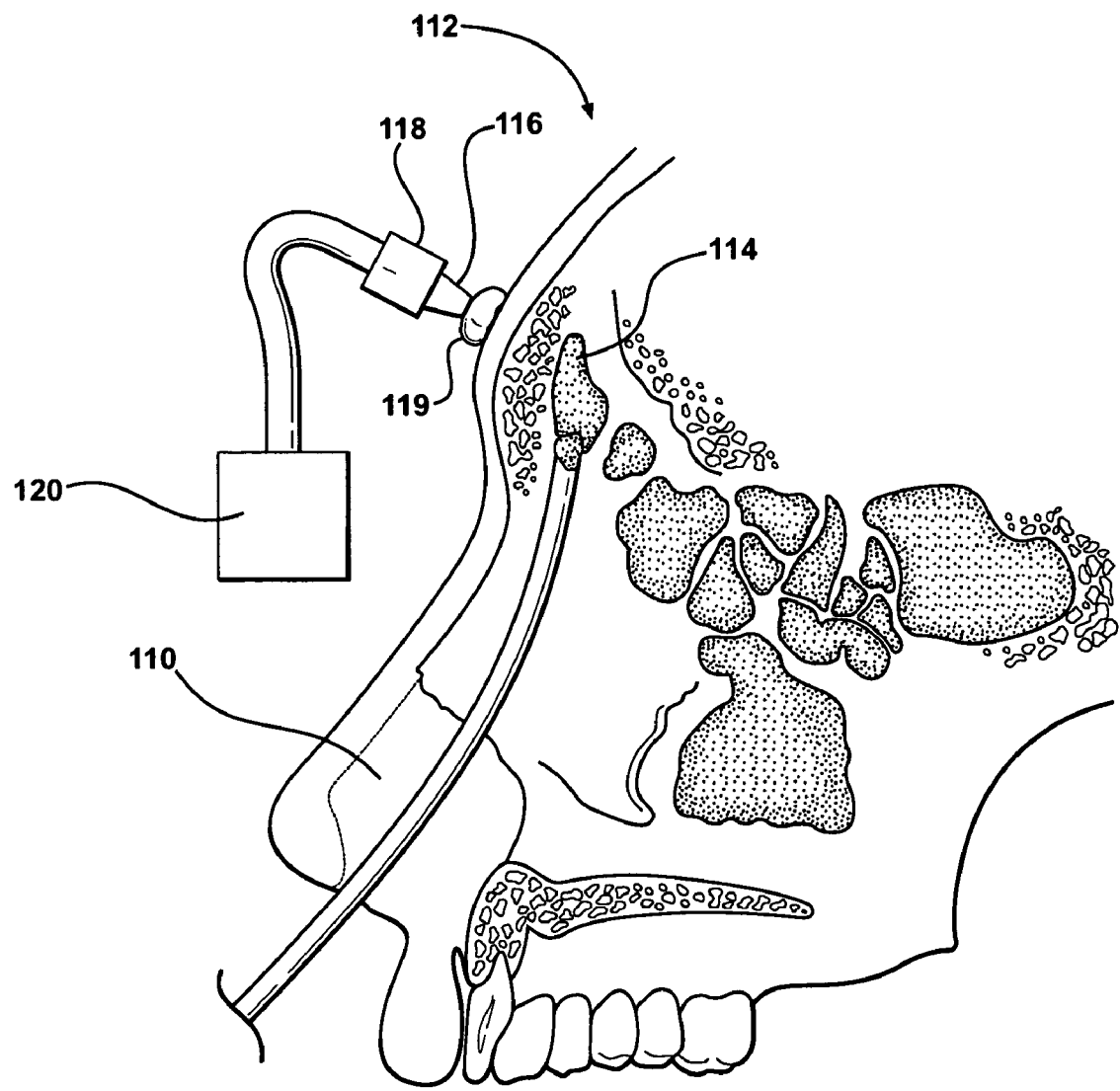
FIG. 9 illustrates a method of treatment of a sinus to remove a biofilm in the mucosal blanket, wherein ultrasonic energy is introduced through the head from a facial probe while the sinus cavity is subjected to irrigation and suction via a probe inserted into the cavity.

When used for the treatment of rhinitis, the tube 14 is applied through the nasal cavity so that its proximal end is adjacent to the sinus area coated with biofilm to be treated. Irrigating fluid is then supplied through lumen 20 and withdrawn through lumen 22 at a suitable rate to maintain a fluid layer over the biofilm area. Ultrasonic energy may be applied through horn 24 to the fluid layer so that forces are imposed on the biofilm. Alternatively, in the embodiment of the invention illustrated in FIG. 9, the ultrasound may be applied separately from the instrument 10 through the patient's body.

The irrigation produces shear forces which tend to tear the protruding sections of the biofilm away and the mechanical agitation produced by the ultrasonic energy enhances this tearing action. The bio-affecting agents in the circulating fluid also act on the biofilm so as to reduce or remove it. The process may require application of combined irrigation and ultrasound for an intended period, such as thirty minutes.

Figure 3:
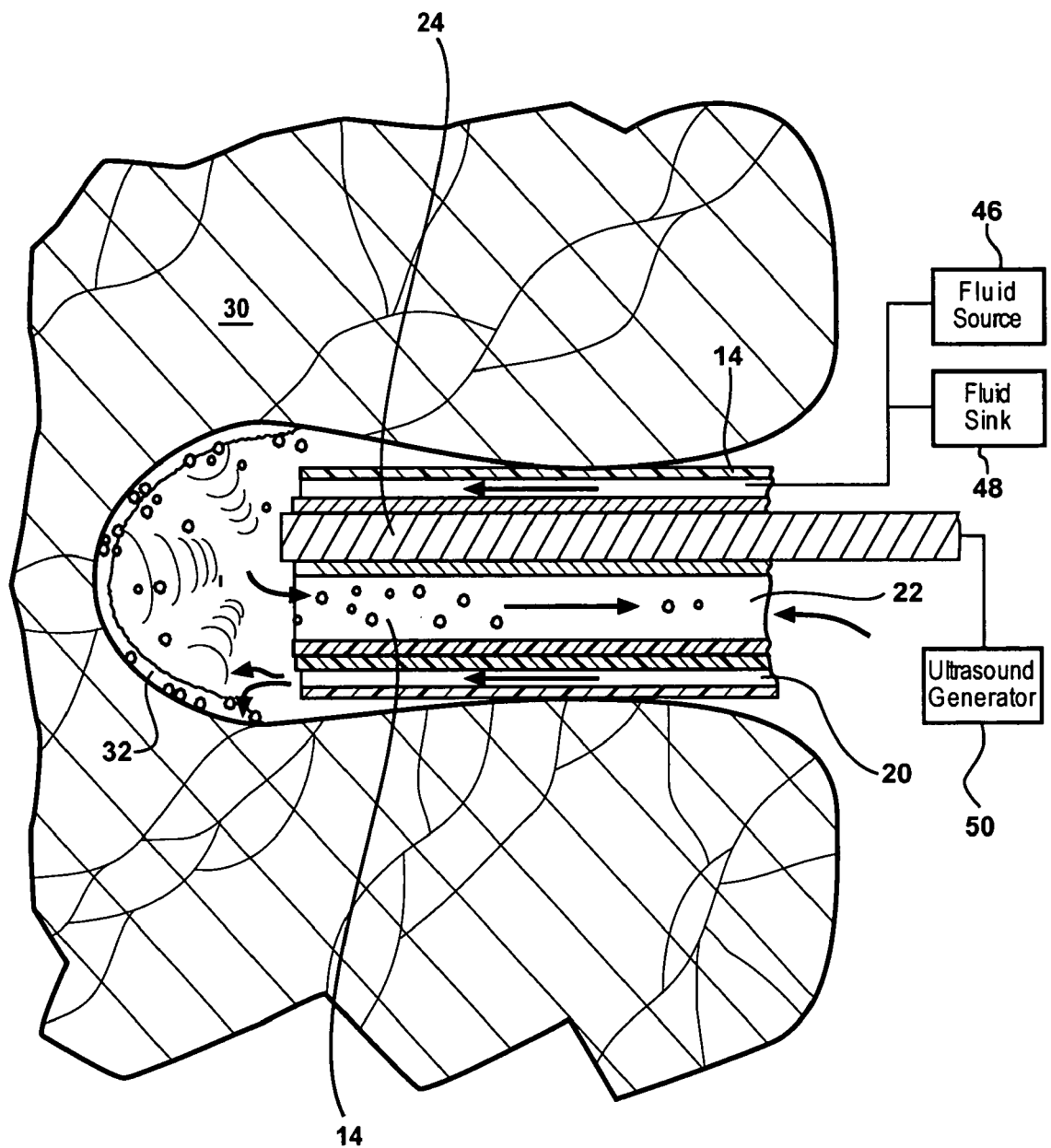
FIG. 3 is a cross-sectional view of the device of FIG. 1 inserted into a living body cavity, with sections broken away to show the construction of the tube.

FIG. 3 illustrates the application of a preferred embodiment of the method of the present invention to a body cavity 30 such as the sinuses. A biofilm coating 32 extends over an infected area, releasing materials which inflame the underlying tissue. Irrigating fluid containing biocides and/or bio-reducing agents are introduced through the lumen 20 from a fluid source 46 and withdrawn from the larger area lumen 22 to a fluid sink 48. Ultrasonic energy is introduced into the fluid film which results from the irrigation via the ultrasonic horn 24 from a generator 44. The biofilm is acted on by the physical shearing forces imposed by the irrigation and suction; by the mechanical forces generated in the overlying fluid film from the ultrasound; and chemical action takes place as a result of the agents contained within the irrigating fluid. These factors reduce or completely eliminate the biofilm so as to free the inflamed area for application of antibiotics and the like which may be contained in the irrigating fluid or may be introduced separately following treatment with the irrigating fluid and ultrasound. The ultrasonic generator 44 provides the energy to the horn either at a set frequency or a scanned frequency or in pulses.

Figure 4:
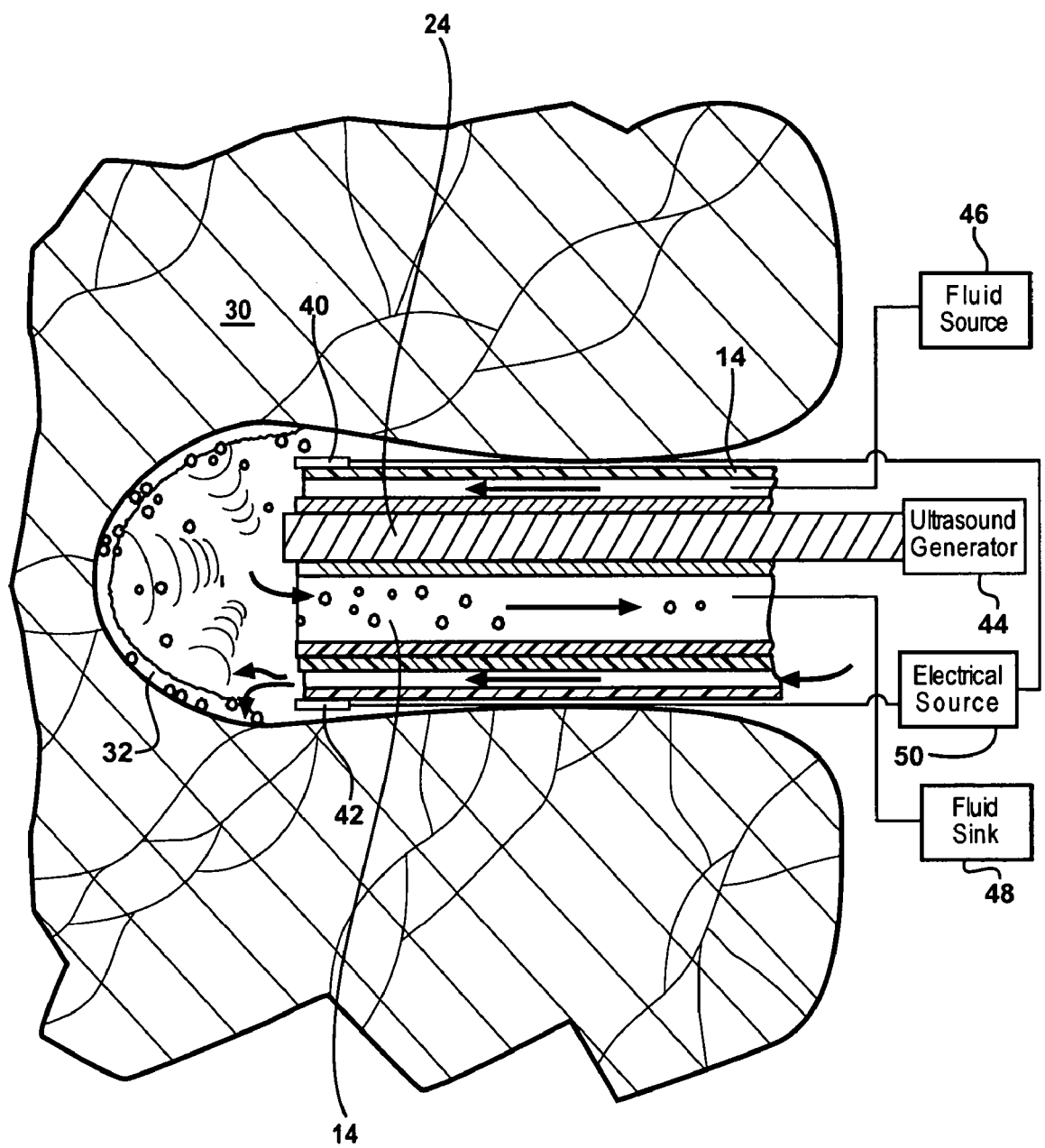
FIG. 4 is a cross-sectional view of an alternative embodiment of the apparatus of the present invention inserted into a living body cavity, and partially broken away to exhibit the electrodes used to impose an electrical field across the biofilm.

FIG. 4 illustrates an alternative embodiment of apparatus capable of imposing an electric field across the biofilm encoating the infected area and/or the fluid layer overlying the biofilm. The structure of the application tube is identical to tile device in FIG. 1 with the exception that a pair of electrodes 40 and 42 extend down diametrically opposed sides of the tube from the proximal end to the distal end. At the proximal end they are connected to an electrical source 50 which generates a potential difference across the electrodes 40 and 42. The applied voltage may be either direct current, either constant or pulsed, or alternating current of a fixed or scanned frequency. The application device also connects to a fluid source 46, a fluid sink 48, and an ultrasound generator 44.

The electric field imposes phoretic forces on the biofilm and may drive the irrigating fluid into the biofilm to enhance disruptive action.

Figure 5:
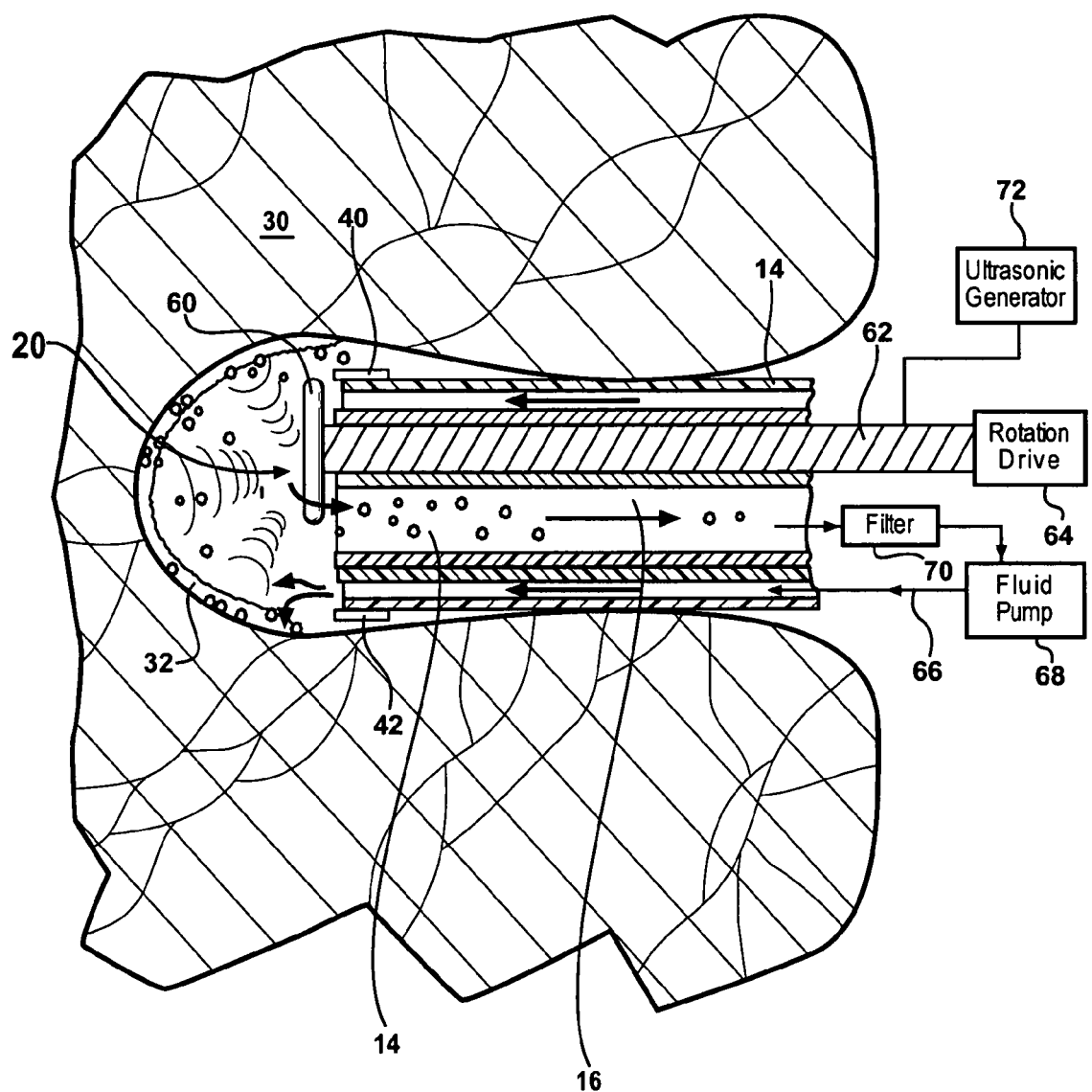
FIG. 5 is a cross-sectional view of another alternative embodiment of the apparatus of the present invention which includes a biofilm abrading device for imparting mechanical energy to the biofilm, supported at the distal end of the tube.

An embodiment of the invention illustrated in FIG. 5 applies mechanical forces to the biofilm through a brush or abrading device 60. The device is either rotated or oscillated through a flexible shaft 62 which extends through the center of the rod 14. At the proximal end it is driven by a drive member 64. Irrigating fluid is provided through a line 66 from a sump to the lumen 20 of the tube 14 and is returned through the lumen 22 to the sump 68 through a filter 70. Ultrasonic forces may also be applied through an ultrasonic horn driven by the generator 72.

Alternatively, the ultrasonic forces could be applied to the proximal end of the fluid column formed in the lumen 20 so that the ultrasonic energy is carried to the distal end 16 by that column, eliminating the need for an ultrasonic horn. The transmission of ultrasonic forces throughout a fluid column is described in ULTRASONICS, VOL. 26, No. 1, 1988 at pages 27-30. The electric field applying electrodes 40 and 42 of the embodiment of FIG. 4 could also be combined with this unit.

Figure 6:
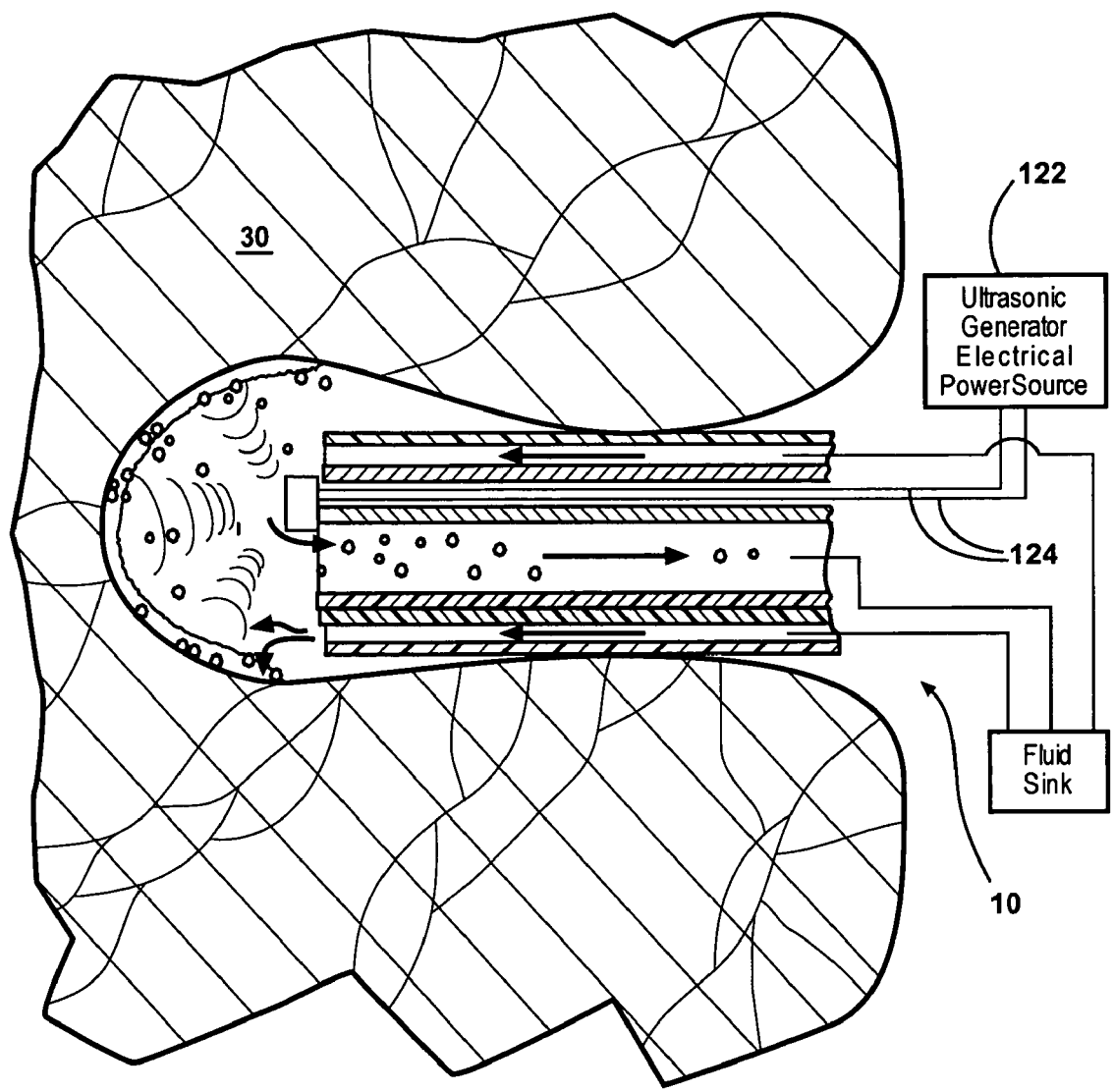
FIG. 6 is a cross-sectional view of an alternative embodiment of the apparatus of the present invention wherein the ultrasonic generator is disposed at the distal end of the instrument.

In another alternative version of the instrument 10, illustrated in FIG. 6, rather than generating the ultrasonic vibrations at the proximal end and transmitting them through the instrument to the distal end, in the manner of the previously described embodiments, a piezoelectric generator 120 is supported at the distal end. Electric signals for powering the generator 120 are provided by a power source 122, located at the proximal end of the instrument 10, and carried to the generator 120 by wires 124 extending through the length of the instrument. This arrangement lightens the weight of the instrument and eliminates the attenuation of the ultrasonic waves which occurs during transmission along the body of the instrument.

The method of the present invention may also be employed on living body tissues that are easily accessible, such as the outer body covered by skin or the mucous membranes of the oral areas. FIG. 7 illustrates an alternative embodiment of the apparatus of the present invention which can be used to treat biofilms formed on these accessible areas. A typical application is to treat a burned portion of the skin over which a biofilm has formed. The apparatus illustrated in FIG. 7 is substantially identical to the embodiment of FIG. 1 except for the provision of a semispherical cavity 80 which is attached to the rod 14 adjacent its distal end 20. The cavity has a central hole through which the distal end of the rod 14 passes so that the open end of the cavity extends beyond the distal end 20. A resilient gasket 82 is formed about the open edge of the cavity 80. By proper manipulation of the tube 14 the gasket may be pressed against an area of the skin to be treated to produce a closed containment volume 84.

The irrigating flow of fluid containing a biocide or other bio-affecting agent from the rod end 14 fills the volume 84 with fluid. As additional fluid is introduced the surplus is sucked off through the second lumen of the rod 14. Ultrasonic energy is then introduced into the fluid through the horn end 16, causing forces to be imposed on the treatment area 86 bounding the volume 84.

A variant of the apparatus used for the treatment of biofilms formed on exterior or otherwise accessible body tissues is illustrated in FIG. 8. A semispherical chamber 92 with a resilient gasket 94 supported on its edge is brought into contact with a region 90 of the body which is coated with biofilm so as to define an enclosed volume 96.

The volume 96 is irrigated by fluid following from an input tube 98 and exiting the volume 96 from an outlet tube 100. The irrigating fluid contains biofilm affecting agents. The resulting fluid in the volume 96 is agitated by ultrasonic waves generated by piezoelectric transducers 102 and 104 spaced on the wall of the enclosure 92 and energized by appropriate electrical signals.

As has been noted, the ultrasonic energy may be introduced into the biofilm by means independent of the fluid flow generated by the irrigation apparatus. In the embodiment of the invention illustrated in FIG. 9, a tube 110 is illustrated as being inserted into the nasal cavity of a human head, generally indicated at 112, so that its distal end is adjacent the frontal sinus 114. The tube 110 contains a pair of lumens for introducing under pressure, and removing under suction, an irrigating fluid, preferably containing a biofilm active agent which is the bio-reducing or biocide drug previously described, onto the mucosal surface covering the exterior of the frontal sinus. The biofilm has the mucosal surface as its substrate and it may become embedded within the mucosal surface.

Simultaneous with the irrigation of the mucosal surface overlying the frontal sinus cavity through the tube 110, ultrasonic energy is introduced into the exterior of the head, proximal to the location of the frontal sinus, through a probe 116 connected to a transducer 118. The probe 116 has a flexible, fluid-filled bag 119 supported on its end. The bag may be filled with a gel, water, or other fluid transparent to ultrasonic energy. The bag prevents skin on the head 112 from being burned by ultrasonic energy. It is positioned in pressured contact with the head to provide an efficient interface.

The transducer 118 is powered by an ultrasonic generator 120. The power levels of the ultrasonic energy are preferably somewhat higher than those provided through the tube 110, because of the attenuation of the energy by the skull bones. The ultrasonic energy reaches the mucosal layer on top of the frontal sinus 114 through the skull and cooperates with the irrigating fluid in a manner similar to the previously described embodiments of the invention.

Alternatively, the ultrasonic energy could be introduced at other locations on the interior of a nasal cavity adjacent to the sinus 114. In the treatment of other biofilms formed at other locations within the human body, similar techniques may be used to provide the ultrasonic energy independent of the irrigating fluid.

Having thus described my invention I claim:

1. The method of reducing a biofilm formed on the mucosal lining of a sinus cavity within a human head, without harming the underlying sinus tissue, comprising:
    irrigating the biofilm formed on the mucosal lining of a sinus cavity with a fluid containing a biofilm-reducing agent;
    suctioning the fluid from the biofilm, so as to maintain a layer of the fluid in contact with the biofilm; and
    inducing ultrasonic energy into the biofilm, through the fluid layer, while performing the suctioning step at a power level which will not affect the underlying tissue;
    whereby the biofilm is disrupted by the forces introduced through the irrigation, suction and ultrasonic agitation, and affected by said agent, and portions of the biofilm are removed with the suctioned fluid, without affecting the underlying tissue.

2. The method of claim 1 further comprising introducing and removing the fluid through an elongated tube having its distal end disposed within the sinus cavity and its proximal end exterior of the body.

3. The method of claim 2 further comprising introducing the ultrasonic energy into the fluid layer through fluid in said elongated tube.

4. The method of claim 1, further comprising: establishing an electric field across the biofilm directly or through the fluid layer.

5. The method of claim 1 wherein the biofilm-reducing agent is chosen from the group consisting of guaifenesin, dornase alfa or N-acetylcysteine or a derivative thereof to simultaneously attack the biofilm and reduce the mucus layer on the sinus lining.

6. The method of claim 1 wherein the biofilm-reducing agent comprises a surfactant.

* * * * *